US008187827B2

(12) United States Patent
Tomosugi

(10) Patent No.: US 8,187,827 B2
(45) Date of Patent: May 29, 2012

(54) DIAGNOSTIC METHODS FOR ACUTE ISCHEMIC DISEASE USING ACTIVATED HEPCIDIN AS AN INDICATOR

(76) Inventor: Naohisa Tomosugi, Ishikawa (JP)

( * ) Notice: Subject to any disclaimer, the term of this patent is extended or adjusted under 35 U.S.C. 154(b) by 0 days.

(21) Appl. No.: 12/601,955

(22) PCT Filed: May 30, 2008

(86) PCT No.: PCT/JP2008/059969
§ 371 (c)(1),
(2), (4) Date: Jun. 10, 2010

(87) PCT Pub. No.: WO2008/146903
PCT Pub. Date: Dec. 4, 2008

(65) Prior Publication Data
US 2010/0298159 A1 Nov. 25, 2010

(30) Foreign Application Priority Data

May 31, 2007 (JP) ................. 2007-145935

(51) Int. Cl.
G01N 33/55 (2006.01)
(52) U.S. Cl. ......................... 435/7.8; 435/7.1
(58) Field of Classification Search .................. None
See application file for complete search history.

(56) References Cited

U.S. PATENT DOCUMENTS

| 7,169,758 | B2 | 1/2007 | Nicolas et al. | |
| 7,320,894 | B2 * | 1/2008 | Kulaksiz et al. | 436/86 |
| 7,411,048 | B2 | 8/2008 | Kulaksiz et al. | |
| 7,416,857 | B2 | 8/2008 | Lehmann et al. | |
| 7,510,842 | B2 * | 3/2009 | Podust et al. | 435/7.1 |
| 7,820,163 | B2 * | 10/2010 | Leung et al. | 424/133.1 |
| 2004/0096987 | A1 | 5/2004 | Geacintov et al. | |
| 2004/0096990 | A1 | 5/2004 | Geacintov et al. | |
| 2005/0136455 | A1 | 6/2005 | Lehmann et al. | |
| 2006/0019339 | A1 | 1/2006 | Lauth et al. | |
| 2007/0124825 | A1 | 5/2007 | Nicolas et al. | |
| 2007/0134746 | A1 | 6/2007 | Kulaksiz et al. | |
| 2009/0173876 | A1 | 7/2009 | Li et al. | |
| 2010/0105067 | A1 | 4/2010 | Fung et al. | |
| 2010/0292131 | A1 * | 11/2010 | Kas et al. | 514/1.4 |
| 2011/0053268 | A1 | 3/2011 | Tomosugi | |

FOREIGN PATENT DOCUMENTS

| JP | 2004-536077 A | 12/2004 |
| JP | 2004536077 A | 12/2004 |
| JP | 2005-128020 A | 5/2005 |
| JP | 2005-134387 A | 5/2005 |
| JP | 2006-517198 A | 7/2006 |
| JP | 2006517198 A | 7/2006 |
| JP | 2008533471 | 8/2008 |
| WO | WO 02/098444 A2 | 12/2002 |
| WO | WO 2006/099126 A2 | 12/2006 |
| WO | WO 2006/135781 A2 | 12/2006 |
| WO | WO 2008/047485 A1 | 4/2008 |

OTHER PUBLICATIONS

Kemna et al. 2008. Haematologica 93:90-97.*
Malyszko et al. Transplantation Proceedings, 2006, 38:2895-2898.*
Merle et al 2007. Endocrinology 148:2663-2668.*
Office Action (Restriction Requirement), U.S. Appl. No. 12/311,842, dated Apr. 7, 2011.
Hishikawa, K., and Iwai, K., "Recent Advance in the Understanding of Iron Metabolism and its Role on Host Defense," Jpn. J. Clin. Immunol 28(6):372-380 (2005), abstract only.
Tomosugi, N., et al., "Detection of Serum Hepcidin in Renal Failure and Inflammation by Using ProteinChip System," downloaded Jul. 8, 2009 http://bloodjournal.hematologylibrary.org/cgi/content/abstract/108/4/1381, Abstract only.
Andrews, N. C., "Molecular Control of Iron Metabolism," *Best Practice & Research Clinical Haematology*, 18(2):159-169 (2005).
Dallalio, G., et al., "Serum Hepcidin in Clinical Specimens," *British Journal of Haematology 122*:996-1000 (2003).
Détivaud, L., et al., "Hepcidin Levels in Humans are Correlated with Hepatic Iron Stores, Hemoglobin Levels, and Hepatic Function," *Blood 106*:746-748 (2005).
Fleming, R.E., "Advances in Understanding the Molecular Basis for the Regulation of Dietary Iron Absorption," *Curr Opin. Gasenterol 21*:201-206 (2005).
Ganz, T., "Hepcidin, a Key Regulator of Iron Metabolism and Mediator of Anemia of Inflammation," *Blood 102*(3):783-788 (2003).
Goss, J.A., et al., "Ischemia-Reperfusion of Rat Liver Modulates Hepcidin in Vivo Expression," *Liver Transplantation 11*(7):800-806 (2005).
Hanawa, H., et al., "Expression of Hepcidin Increases in Cardiomyocytes Under Myocarditis and Myocardial Infarction," *Circulation Journal 72*(Suppl. I):511 (#PJ-007) (2008). Hunter, H.N., et al., "The Solution Structure of Human Hepcidin, a Peptide Hormone With Antimicrobial Activity That is Involved in Iron Uptake and Hereditary Hemochromatosis," *J. of Biol. Chem. 277*(40):37597-37603 (2002).
Kemna, E., et al., "Novel Urine Hepcidin Assay by Mass Spectrometry," *Blood 106*:3268-3270 (2005).
Krause, A., et al., "LEAP-1, a Novel Highly Disulfide-Bonded Human Peptide, Exhibits Antimicrobial Activity," *FEBS Letters 480*:147-150 (2000).
Kulaksiz, H., et al., "Pro-hepcidin: Expression and Cell Specific Localisation in the Liver and its Regulation in Hereditary Haemochromatosis, Chronic and Renal Insufficiency, and Renal Anaemia," *Gut 53*:735-743 (2004).

(Continued)

*Primary Examiner* — Shulamith H Shafer
(74) *Attorney, Agent, or Firm* — Hamilton, Brook, Smith & Reynolds, P.C.

(57) ABSTRACT

An objective of the present invention is to provide methods of testing for acute ischemic diseases using active hepcidin as an indicator, methods for determining the timing to administer an agent for treating the disease, and kits for these methods. To accomplish the objective, the present inventors analyzed the serum proteome patterns characteristic of acute myocardial infarction patients using SELDI-TOF-MS. As a result, it was found that hepcidin-20 has a very high correlation with acute myocardial infarction. Furthermore, the present inventors discovered that at the time of disease onset, the blood concentration of hepcidin-20 rises sharply in particular, and shows high levels within six hours, especially four hours of onset. The present invention enables early diagnosis of acute ischemic diseases.

10 Claims, 3 Drawing Sheets

OTHER PUBLICATIONS

Malyszko, J., et al., "Hepcidin, an Acute-Phase Protein and a Marker of Inflammation in Kidney Transplant Recipients With and Without Coronary Artery Disease," *Transplantation Proceedings* 38:2895-2898 (2006).

National Kidney Foundation, Inc., "NKF-DOQI Clinical Practice Guidelines for the Treatment of Anemia of Chronic Renal Failure," *American Journal of Kidney Diseases* 30(4) (Suppl 3):S194-S240 (1997).

Nemeth, E., et al., "Hepcidin, a Putative Mediator of Anemia of Inflammation, is a Type II Acute-Phase Protein," *Blood* 101(7):2461-2463 (2003).

Nemeth, E., et al., "IL-6 Mediates Hypoferremia of Inflammation by Inducing the Synthesis of the Iron Regulatory Hormone Hepcidin," *The Journal of Clinical Investigation* 113(9):1271-1276 (2004).

Nicolas, G., et al., "The Gene Encoding the Iron Regulatory Peptide Hepcidin is Regulated by Anemia, Hyopxia, and Inflammation," *The Journal of Clinical Investigation* 110(7):1037-1044 (2002).

Park, C.H., et al., "Hepcidin, a Urinary Antimicrobial Peptide Synthesized in the Liver," *The Journal of Biological Chemistry* 276(11):7806-7810 (2001).

Petricoin, III, E.F., et al., "Use of Proteomic Patterns in Serum to Identify Ovarian Cancer," *The Lancet*, 359:572-577 (2002).

Philpott, C.C., "Molecular Aspects of Iron Absorption: Insights Into the Role of HFE in Hemochromatosis,"*Hepatology* 35:993-1001 (2002).

Pigeon, C., et al., "A New Mouse Liver-specific Gene, Encoding a Protein Homologous to Human Antimicrobial Peptide Hepcidin, Is Overexpressed During Iron Overload," *The Journal of Biological Chemistry*, 276(11):7811-7819 (2001).

Sanchez, J.-C., et al., "Cystatin C as a Potential Cerebrospinal Fluid Marker for the Diagnosis of Creutzfeldt-Jakob Disease," *Proteomics* 4:2229-2233 (2004).

Stanley, B.A., "Heart Disease, Clinical Proteomics and Mass Spectrometry," *Disease Markers* 20:167-178 (2004).

Taes, Y.E.C., et al., "Prohepcidin Accumulates in Renal Insufficiency," *Clin Chem Lab Med* 42(4):387-389 (2004).

Tomosugi, N., et al., "Detection of Serum Hepcidin in Renal Failure and Inflammation by Using ProteinChip System," *Blood* 108:1381-1387 (2006).

Tomosugi, N., et al., "Diagnostic Potential of Tear Proteomic Patterns in Sjögren's Syndrome," *Journal of Proteome Research* 4:820-825 (2005).

Tsuchiya, et al., "Tetsu Taisha Kanren Tanpaku Hepcidin Hatsugen Ni Eikyo O Oyobosu lnshi No Kento," $50^{th}$ *Annual Meeting of the Japanese Society for Dialysis Therapy*, O-1722:785 (2005).

International Search Report, PCT/JP2008/059969; Date Mailed: Jul. 1, 2008.

Notification of Transmittal of Translation of the International Preliminary Report on Patentability (IPRP) with IPRP, PCT/JP2008/059969, mailed Jan. 21, 2010.

Kawabata, H., et al., Hepcidin-Saikin no Shinpo, ketsueki, Shuyoka, 51(2):174-182 (2005).

Henderson, N. A. and Steele, R.J.C., "SELDI-TOF Proteomic Analysis and Cancer Detection", Surgeon 3(6):383-390 (2005).

Means, Jr., R.T., "Hepcidin and Anaemia", Blood Reviews 18:219-225 (2004).

Swinkels, D.W., et al. "Advances in Quantitative Hepcidin Measurements by Time-of-Flight Mass Spectrometry", PLoS One 3(7):1-7 (2008).

Tsuchiya, et al., "Tetsu Taisha Kanren Tanpaku Hepcidin Hatsugen Ni Eikyo O Oyobosu lnshi No Kento," 50th Annual Meeting of the Japanese Society for Dialysis Therapy, O-1722:785 (2005) English Translation.

Reply, U.S. Appl. No. 12/311,842, filed Jun. 7, 2011.

Office Action, U.S. Appl. No. 12/311,842, dated Jul. 18, 2011.

Notification of Transmittal of Translation of the International Preliminary Report on Patentability (IPRP) with IPRP, Written Opinion and International Search Report, PCT/JP2007/055361, mailed Apr. 30, 2009.

* cited by examiner

SEQUENCE LISTING

<160> NUMBER OF SEQ ID NOS: 5

<210> SEQ ID NO 1
<211> LENGTH: 20
<212> TYPE: PRT
<213> ORGANISM: Homo sapiens

<400> SEQUENCE: 1

Ile Cys Ile Phe Cys Cys Gly Cys Cys His Arg Ser Lys Cys Gly Met
 1               5                   10                  15

Cys Cys Lys Thr
            20

```
<210> SEQ ID NO 2
<211> LENGTH: 25
<212> TYPE: PRT
<213> ORGANISM: Homo Sapiens

<400> SEQUENCE: 2

Asp Thr His Phe Pro Ile Cys Ile Phe Cys Cys Gly Cys Cys His Arg
 1               5                  10                  15

Ser Lys Cys Gly Met Cys Cys Lys Thr
            20                  25

<210> SEQ ID NO 3
<211> LENGTH: 25
<212> TYPE: PRT
<213> ORGANISM: Rattus norvegicus

<400> SEQUENCE: 3

Asp Thr Asn Phe Pro Ile Cys Leu Phe Cys Cys Lys Cys Cys Lys Asn
 1               5                  10                  15

Ser Ser Cys Gly Leu Cys Cys Ile Thr
            20                  25

<210> SEQ ID NO 4
<211> LENGTH: 25
<212> TYPE: PRT
<213> ORGANISM: Mus musculus

<400> SEQUENCE: 4

Asp Thr Asn Phe Pro Ile Cys Ile Phe Cys Cys Lys Cys Cys Asn Asn
 1               5                  10                  15

Ser Gln Cys Gly Ile Cys Cys Lys Thr
            20                  25

<210> SEQ ID NO 5
<211> LENGTH: 25
<212> TYPE: PRT
<213> ORGANISM: Mus musculus

<400> SEQUENCE: 5

Asp Ile Asn Phe Pro Ile Cys Arg Phe Cys Cys Gln Cys Cys Asn Lys
 1               5                  10                  15

Pro Ser Cys Gly Ile Cys Cys Glu Glu
            20                  25
```

DIAGNOSTIC METHODS FOR ACUTE ISCHEMIC DISEASE USING ACTIVATED HEPCIDIN AS AN INDICATOR

RELATED APPLICATIONS

This application is the U.S. National Stage of International Application No. PCT/JP2008/059969, filed May 30, 2008, which designates the U.S., published in Japanese, and claims priority under 35 U.S.C. §§119 or 365(c) to Japan Application No. JP2007/145935, filed May 31, 2007.

BACKGROUND OF THE INVENTION

The current understanding of the regulation of iron metabolism is based on the biology of a number of critical proteins, which include transferrin, transferrin receptors, ferritin, iron regulatory proteins, divalent metal transporter 1, ferroportin, and hepcidin (Non-patent Documents 1 to 4). Among these factors, plasma transferrin and ferritin are generally measured in the laboratory as an indicator of the total iron binding capacity and overall iron storage, respectively. The peptide hepcidin, which is produced by the liver, controls plasma iron levels by regulating the absorption of food iron from the intestine as well as the release of iron from macrophages. Furthermore, hepcidin is also an acute-phase reactant with antimicrobial activity induced by inflammation (Non-patent Documents 5 to 7). Most studies that confirm the role of hepcidin in iron metabolism, inflammation, anemia, and hypoxia were performed in vitro or using experimental mice (Non-patent Documents 5 and 8); therefore, its role in human diseases is unclear.

Renal anemia in hemodialysis patients can be clinically alleviated by the administration of human recombinant erythropoietin (Non-patent Document 9); however, the exact mechanism of iron metabolism in these patients is largely unknown. In several clinical studies, the amount of hepcidin was estimated based on the levels of prohepcidin in urine (Non-patent Documents 6 to 10 and 13) or serum (Non-patent Documents 14 to 16) or based on the levels of mRNA expression in the liver (Non-patent Document 10); however, it has been reported that serum prohepcidin concentration does not clearly correlate with any red cell indices or with iron status (Non-patent Document 14) and that the concentration of prohepcidin may increase because of its accumulation. In addition, prohepcidin, which is measured by enzyme-linked immunosorbent assay (ELISA), is not bioactive and no specific function has been identified. Hepcidin-20, -22, and -25, which are cleaved from prohepcidin by convertases, are the active forms of prohepcidin (Non-patent Document 6); however, there are few reports on the quantitative evaluation of the bioactive forms of hepcidin, primarily because of difficulties involved in the development of specific antibodies against these bioactive forms of hepcidin, which have compact folded structures (Non-patent Document 17).

Hepcidin, which is a key regulator of iron metabolism, is expressed in the liver, distributed in blood, and excreted in urine. To date, some diagnostic methods using hepcidin as an indicator have been reported (Patent Documents 1 to 4); however, no reliable and practical method for the measurement of the bioactive forms of hepcidin in serum has been developed.

The SELDI-based ProteinChip System® (Ciphergen Biosystems, Inc., Fremont, Calif., USA) array technology has been successfully used to detect relevant biomarkers in a wide variety of diseases, which include immunological conditions, cancer, neurological conditions, cardiovascular conditions, and diseases of the lacrimal gland (Non-patent Documents 18 to 21). SELDI technology is based on a classical solid-phase extraction chromatography method combined with direct laser desorption/ionization mass spectrometric detection and requires minimal amounts of biological fluid, without pretreatment. This technology enables the evaluation of the subtle differences between disease and control states in the expression of individual proteins or groups of proteins in various fluids, which include serum, urine, tears, and cerebrospinal fluid. Furthermore, it has a number of advantages, which include high-throughput capability, very high sensitivity for the detection of proteins in the picomole to femtomole ranges, high resolution for low-molecular-weight proteins (i.e., below 20 kDa), and facility of operation.

Generally, hepcidin-20 is known as an antimicrobial peptide (Non-patent Document 22), and hepcidin-25 is known as an iron-regulatory peptide (Non-patent Document 23).

In recent years, the use of the above-mentioned SELDI-TOF MS has enabled semi-quantitative measurement of hepcidin-20 and -25 in the serum, and it has been reported that hepcidin-20 and -25 of hemodialysis patients show significant correlation with the level of serum ferritin, and that hepcidin-25 accumulates in the serum of hemodialysis patients. Furthermore, it has been reported that active hepcidin, particularly hepcidin-25, may be contributing to the etiology of renal anemia (Non-patent Document 24).

However, there are no reports on the association of hepcidin, or particularly the association of hepcidin-20, with acute ischemic diseases.

Documents of related prior arts for the present invention are described below.

Non-patent Document 1: Andrews N C. Best Pract Res Clin Haematol. 2005; 18:159-169.
Non-patent Document 2: Philpott C C. Hepatology. 2002; 35:993-1001.
Non-patent Document 3: Fleming R E. Curr Opin Gastroenterol. 2005; 21:201-206.
Non-patent Document 4: Ganz T. Blood. 2003; 102:783-788.
Non-patent Document 5: Pigeon C, Ilyin G, Courselaud B, et al. J Biol Chem. 2001 16; 276:7811-7819.
Non-patent Document 6: Park C H, Valore E V, Waring A J, Ganz T. J Biol Chem. 2001; 276:7806-7810.
Non-patent Document 7: Krause A, Neitz S, Magert H J, et al. FEBS Lett. 2000; 480:147-150.
Non-patent Document 8: Nicolas G, Chauvet C, Viatte L, et al. J Clin Invest. 2002; 110:1037-1044.
Non-patent Document 9: National Kidney Foundation. Am J Kidney Dis. 1997; 30(Suppl 3):S192-240.
Non-patent Document 10: Detivaud L, Nemeth E, Boudjema K, et al. Blood. 2005; 106:746-748.
Non-patent Document 11: Kemna E, Tjalsma H, Laarakkers C, Nemeth E, Willems H, Swinkels D. Blood. 2005 Jul. 19; [Epub ahead of print]
Non-patent Document 12: Nemeth E, Rivera S, Gabayan V, et al. J Clin Invest. 2004; 113:1271-1276.
Non-patent Document 13: Nemeth E, Valore E V, Territo M, Schiller G, Lichtenstein A, Ganz T. Blood. 2003; 101:2461-2463.
Non-patent Document 14: Taes Y E, Wuyts B, Boelaert J R, De Vriese A S, Delanghe J R. Clin Chem Lab Med. 2004; 42:387-389.
Non-patent Document 15: Kulaksiz H, Gehrke S G, Janetzko A, et al. Gut. 2004 May; 53(5):735-743.
Non-patent Document 16: Dallalio G, Fleury T, Means R T. Br J. Haematol. 2003; 122:996-1000.
Non-patent Document 17: Hunter H N, Fulton D B, Ganz T, Vogel H J. J Biol Chem. 2002; 277:37597-37603.

Non-patent Document 18: Petricoin E F, Ardekani A M, Hitt B A, et al. Lancet. 2002; 359:572-577.
Non-patent Document 19: Sanchez J C, Guillaume E, Lescuyer P, et al. Proteomics. 2004; 4:2229-2233.
Non-patent Document 20: Stanley B A, Gundry R L, Cotter R J, Van Eyk J E. Dis Markers. 2004; 20:167-178.
Non-patent Document 21: Tomosugi N, Kitagawa K, Takahashi N, Sugai S, Ishikawa I. J Proteome Res. 2005; 4:820-825.
Non-patent Document 22: Krause A, FEBS LETT. 2000 Sep. 1; 480(2-3):147-50.
Non-patent Document 23: Park C H, J Biol Chem. 2001 Mar. 16; 276(11):7806-10. Epub 2000 Dec. 11
Non-patent Document 24: Tomosugi N, Blood. 2006 Aug. 15; 108(4):1381-7. Epub 2006 Apr. 18.
Patent Document 1: Japanese Patent Application Kokai Publication No. (JP-A) 2005-134387 (unexamined, published Japanese patent application)
Patent Document 2: US 2004/0096987 A1
Patent Document 3: US 2004/0096990 A1

BRIEF SUMMARY OF THE INVENTION

The present invention relates to methods for diagnosis of acute ischemic disease using active hepcidin as an indicator.

DETAILED DESCRIPTION OF THE INVENTION

Figure 1:
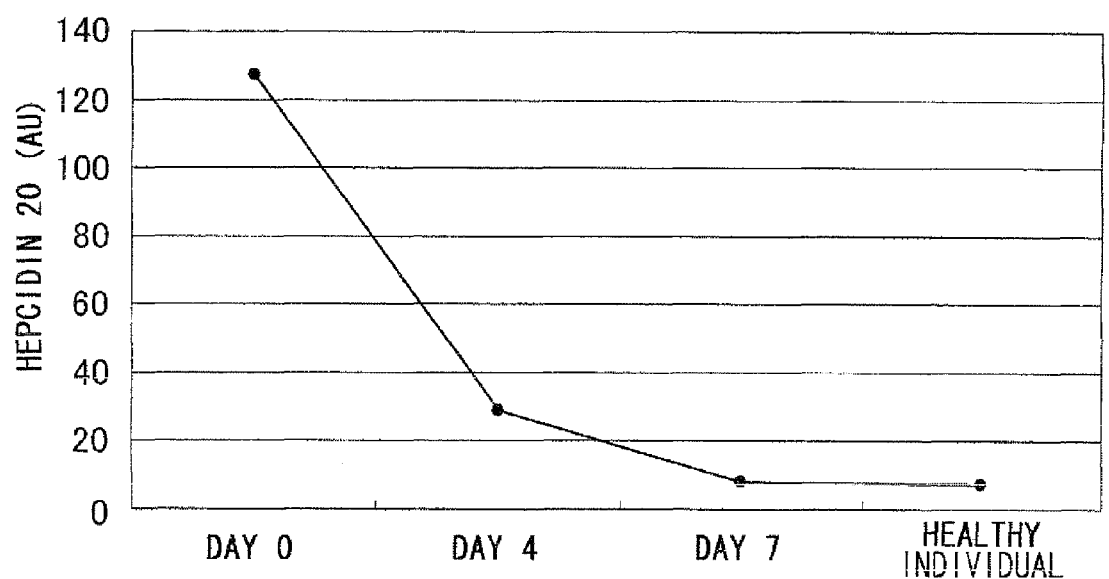
FIG. 1 shows the mean values for the time-dependent change of hepcidin-20 intensity in acute myocardial infarction patients.

[Problems to be Solved by the Invention]

An objective of the present invention is to discover marker proteins for acute ischemic disease and to provide inventions using the marker proteins. More specifically, an objective of the present invention is to provide methods of testing for acute ischemic diseases using active hepcidin as an indicator, methods for determining the timing to administer an agent used for treating the disease, and kits to be used in these methods.

[Means for Solving the Problems]

To accomplish the above-mentioned objectives, the present inventors analyzed the serum proteome patterns characteristic of acute myocardial infarction patients using surface-enhanced laser desorption/ionization time-of-flight mass spectrometry (SELDI-TOF-MS). As a result, hepcidin-20 was found to have a very high correlation with acute myocardial infarction, and this correlation was higher than hepcidin-25. This result contradicts the expectation since hepcidin-20 has been considered as an antimicrobial peptide and hepcidin-25 as an iron-regulatory peptide.

Furthermore, the present inventors discovered that at the time of disease onset, the blood concentration of hepcidin-20 rises sharply in particular, and shows high levels six hours, especially four hours, and furthermore 3.5 hours within onset. Therefore, they discovered that it is possible to diagnose acute ischemic diseases early by measuring the level of hepcidin in blood.

More specifically, the present invention provides the following [1] to [9].

[1] A method of testing for an acute ischemic disease, which comprises the step of measuring the amount of active hepcidin in a sample collected from a subject.
[2] A method for determining the timing to administer an agent for treating acute ischemic disease, which comprises the step of measuring the amount of active hepcidin in a sample collected from a subject over time.
[3] A method for selecting an optimal agent for treating acute ischemic disease, which comprises the steps of:
(a) measuring the amount of active hepcidin in a sample collected from a subject administered with a test agent;
(b) processing one or more test agents different from the test agent used in step (a) individually in the same way as in step (a);
(c) comparing the individual amounts of active hepcidin measured in step (a) and step (b) with that in a control sample; and
(d) selecting a test agent that brings the amount of active hepcidin closest to that in the control sample based on the comparison result obtained in step (c).
[4] The method of any one of [1] to [3], wherein the active hepcidin is hepcidin-20.
[5] The method of any one of [1] to [4], wherein the acute ischemic disease is acute ischemic heart disease.
[6] The method of [5], wherein the acute ischemic heart disease is acute myocardial infarction.
[7] The method of [6], wherein the acute myocardial infarction is acute myocardial infarction within six hours of onset.
[8] The method of any one of [1] to [7], wherein the sample collected from the subject is any of plasma, serum, blood, urine, and tissue extract.
[9] A kit for use in the method of any one of [1] to [8].

[Mode for Carrying Out the Invention]

The present inventors discovered that active hepcidin is a marker protein for acute ischemic diseases, and thereby discovered that early diagnosis of acute ischemic diseases is possible. The present invention is based on these findings.

The present invention provides methods of testing for an acute ischemic disease, which comprise the step of measuring the amount of active hepcidin in a sample collected from a subject.

In the test methods of the present invention, when the sample collected from a subject has a greater amount of active hepcidin than a control sample, the subject is determined or diagnosed as having developed an acute ischemic disease.

Herein, the control sample includes, for example, a sample collected from a healthy individual.

When a subject is human, in general, medical practitioners (including persons who are instructed by medical practitioners; the same applies henceforth) diagnose such diseases. The data obtained on the quantity of active hepcidin by using the test methods of the present invention are useful to medical practitioners in diagnosis. Therefore, the test methods of the present invention may also be described as methods for collecting and presenting useful data to medical practitioners for diagnosis.

Furthermore, the present invention provides methods for determining the timing to administer agents used for treating acute ischemic diseases, which comprise the step of measuring the amount of active hepcidin in samples collected from subjects over time.

In the methods of the present invention for determining the timing to administer agents, the time when the measured amount of active hepcidin is increased compared with that in a healthy individual is determined to be the time for agent administration. Furthermore, when the amount of active hepcidin measured after administering the aforementioned agent is increased or shows no change when compared with that in the initial measurement, it is determined to be the time for administering the agent.

When the subject is human, in general, medical practitioners determine the timing for administration of agents. The data obtained by using the methods of the present invention for determining the timing to administer agents are useful when medical practitioners determine the timing of agent administration. Therefore, the methods of the present invention for determining the timing to administer agents may also be described as methods for collecting and presenting useful data to medical practitioners for determining the timing of agent administration.

In the methods of the present invention for determining the timing of agent administration, the subjects include, for example, those who have developed an acute ischemic disease.

In addition, the present invention provides methods for determining the dose of an agent used for treating acute ischemic diseases, which comprise the step of measuring the amount of active hepcidin in each sample collected from a subject over time.

In the methods of the present invention for determining the dose of an agent, when the amount of active hepcidin measured after administering the aforementioned agent changes compared with that in a healthy individual or in the initial measurement, it can be determined whether the dose is appropriate or not. More specifically, when the amount of active hepcidin after administration of the aforementioned agent is decreased compared with that in a healthy individual or in the initial measurement, it can be determined that the dose is appropriate.

When the subject is human, in general, medical practitioners determine the dose of an agent. The data obtained using the methods of the present invention for determining the dose of an agent are useful to medical practitioners in determining the dose of an agent. Therefore, the methods of the present invention for determining the dose of an agent can also be described as methods for collecting and presenting useful data to medical practitioners for determining the dose of an agent.

In the methods of the present invention for determining the dose of an agent, the subjects include, for example, those who have developed an acute ischemic disease.

In addition, the present invention provides a method for selecting an optimal agent for treating acute ischemic disease, which comprises the steps of:

(a) measuring the amount of active hepcidin in a sample collected from a subject administered with a test agent;

(b) processing one or more test agents different from the test agent used in step (a) individually in the same way as in step (a);

(c) comparing the amount of each active hepcidin measured in step (a) and step (b) with that in a control sample; and (d) selecting a test agent that brings the amount of active hepcidin closest to that in the control sample, based on the comparison result obtained in step (c).

When the subject is human, in general, medical practitioners select an optimal agent for treatment of such diseases. The data obtained using the methods of the present invention for agent selection are useful to medical practitioners in selecting such agents. Therefore, the methods of the present invention for agent selection can also be described as methods for collecting and presenting useful data to medical practitioners for selecting agents.

In the methods of the present invention for agent selection, each test agent is administered to the same subject. An optimal agent can be selected from multiple types (two or more types) of test agents by performing the methods of the present invention for agent selection.

More specifically, the methods of the present invention for agent selection are methods for selecting an optimal agent to treat subjects that have developed an acute ischemic disease and who have an increased amount of active hepcidin, which comprise the steps of:

(1) measuring the amount of active hepcidin in a sample collected from a subject administered with a test agent;

(2) processing one or more test agents different from the test agent used in step (1) individually in the same way as in step (1);

(3) comparing the amount of each active hepcidin measured in step (1) and step (2) with that in a control sample; and (4) selecting a test agent that reduces active hepcidin to an amount closest to that in the control sample based on the comparison result obtained in step (3).

In the methods of the present invention for agent selection, methods for determining the timing to administer an agent, and methods for determining the dose of an agent, the test agent includes known agents for the treatment of acute ischemic diseases. Such therapeutic agents include, for example, erythropoietin, thrombolytic agents, nitrates, adrenergic β receptor blockers, and calcium antagonists, but are not limited thereto.

Thrombolytic agents preferably include, for example, urokinase and t-PA.

Nitrates preferably include, for example, nitroglycerin, isosorbide mononitrate, amyl nitrite, and nicorandil.

Adrenergic β receptor blockers preferably include, for example, propranolol, alprenolol, indenolol, oxprenolol, bunitrolol, bufetolol, bupranolol, bucumolol, pindolol, carteolol, timolol, nadolol, tilisolol, acebutolol, celiprolol, metoprolol, atenolol, bisoprolol, betaxolol, carvedilol, arotinolol, and nipradilol.

Calcium antagonists preferably include, for example, diltiazem, verapamil, nifedipine, nisoldipine, nitrendipine, efonidipine, and amlodipine.

Herein, "active hepcidin" refers to hepcidin-20 (polypeptide comprising the amino acid sequence of SEQ ID NO: 1) and/or hepcidin-25 (polypeptide comprising the amino acid sequence of SEQ ID NO: 2), for example, when the target or subject is a human. Alternatively, "active hepcidin" herein refers to hepcidin (polypeptide comprising the amino acid sequence of SEQ ID NO: 3) when the target or subject is a rat, or to hepcidin-1 (polypeptide comprising the amino acid sequence of SEQ ID NO: 4) and/or hepcidin-2 (polypeptide comprising the amino acid sequence of SEQ ID NO: 5) when the target or subject is a mouse.

Herein, "active hepcidin" is preferably hepcidin-20 or hepcidin-25, and more preferably hepcidin-20.

In the present invention, "acute ischemic disease" includes acute injury, rejection at the time of transplantation, ischemic cerebrovascular disease (apoplexy, cerebral infarction, etc.), ischemic renal disease, ischemic lung disease, ischemic disease related to infection, ischemic disease of the limbs, and ischemic heart disease (ischemic cardiomyopathy, myocardial infarct, ischemic heart failure, etc.). Examples of acute ischemic disease in the present invention are preferably acute ischemic heart disease, and more preferably acute ischemic myocardial infarction.

Furthermore, it is preferable that the above-mentioned acute ischemic disease in the diagnostic methods of the present invention is one day, preferably twelve hours, more preferably six hours, even more preferably four hours, yet even more preferably 3.5 hours, and most preferably 2.5 hours within onset.

Samples collected from subjects and used in the methods of the present invention include, for example, plasma, serum, blood, urine, or tissue extract, but are preferably serum. For example, when the subject is human and the sample is serum, methods of the present invention are conducted using serum samples or blood prepared by medical facilities. In the latter case, persons who conduct the methods of the present invention can prepare serum samples from blood using methods known to those skilled in the art. For example, collected blood are centrifuged and the sera are collected. The resulting sera can be used as samples after dilution to an appropriate concentration, without special pretreatment.

In the present invention, the preferred subjects or targets are humans, rats, and mice, but are not limited thereto. The subjects or targets also include nonhuman animals; for example: monkeys, bovines, sheep, dogs, cats, and hamsters.

In the methods of the present invention, the "step of measuring the amount of active hepcidin in a sample collected from subjects" comprises, for example, the steps of:
(a) mixing a sample with a carrier having the property of binding to the active forms of (1) hepcidin-20 and/or (2) hepcidin-25; and
(b) measuring the amount of active hepcidin bound to the carrier.

The step described above in (a) is preferably conducted under conditions where the above-described carrier only binds polypeptides whose substantial pI value is 8 or more. For example, a chip with cation exchange groups, such as CM10, may be used. The step can be carried out by contacting the chip with diluted samples at or above pH 8 and then washing the chip with a washing buffer at or above pH 8. The noise in the measurement of active hepcidin can be reduced by adjusting polypeptides with a pI greater than or equal to 8 to have positive charges. This renders more accurate and simpler diagnosis of acute ischemic diseases, and selection of the timing to administer agents for treating acute ischemic diseases and the optimal agents for treatment of subjects with acute ischemic disease. The preferred pI is 9.2 or greater and a pI of 10 or higher is more preferred.

Such methods include, for example, mass spectrometry. Mass spectrometry includes, for example, SELDI-TOF-MS and MALDI-TOF-TOF. SELDI-TOF-MS is preferred.

SELDI-TOF-MS is a method that comprises immobilizing carriers onto the surface of a chip to be used in a time-of-flight mass spectrometer; contacting test samples with the chip surface with immobilized carriers; washing the chip under an appropriate condition; and measuring the mass of proteins trapped onto the chip surface using the time-of-flight mass spectrometer.

SELDI-TOF-MS is an abbreviation of time-of-flight mass spectrography (TOF-MS) using surface-enhanced laser desorption/ionization (SELDI).

Chips with immobilized carriers on their surface are generally referred to as protein chips. In the present invention, protein chips include, for example, chemical chips with chemical properties such as hydrophobic type, cation exchange type, anion exchange type, metal ion type, or normal phase type; activated chips for the analysis of specific binding (interaction); and biological chips of the antibody, receptor, or DNA type. Preferred chips are chemical chips with immobilized cation exchange groups (more preferably CM10), chemical chips with immobilized metal ions (more preferably IMAC30-Cu), or chemical chips with immobilized hydrophobic groups (more preferably H4). CM10 is a chip with immobilized carboxymethyl groups on its surface. IMAC30-Cu is a chip with immobilized NTA on its surface. H4 is a chip that has the same binding property as that of the C16 reverse phase column.

Alternatively, biological chips with immobilized antibodies that bind to hepcidin-20 or hepcidin-25 can also be used in the present invention. In general, antibodies are immobilized onto chips via carbonyldiimidazole or activated epoxy groups.

SELDI-TOF-MS generally comprises steps (1) to (5) described below; however, SELDI-TOF-MS in the present invention is not limited to methods comprising these steps, as long as they allow the detection of active hepcidin.

(1) Step of Adding Samples onto a Protein Chip

A sample diluted with a buffer (20 times diluted serum in this Example) is applied to a protein chip. The chip is incubated (for 30 min in this Example).

(2) Step of Washing the Protein Chip after Sample Application

The chip surface is washed to remove proteins and other molecules that are not bound to the chip surface.

(3) Step of Applying Energy Absorption Molecules (EAMs) to the Protein Chip after Washing To enhance the ionization of proteins trapped onto the chip surface, energy absorption molecules (EAMs) are injected and the chip is dried. In the present invention, EAM denotes molecules that are capable of absorbing energy from a laser desorption/ionization source and, thereafter, contribute to desorption and ionization of analyte molecules in contact therewith. EAMs of the present invention are not particularly limited, as long as it can be used in the protein chip system. EAMs include, for example, cinnamic acid derivatives, sinapinic acid (SPA), cyanohydroxy cinnamic acid (CHCA) and dihydroxybenzoic acid, ferulic acid, and hydroxyacetophenone derivatives. A preferred EAM is CHCA.

The noise in the measurement of active hepcidin can be reduced by removing polypeptides as much as possible other than polypeptides with pI of 8 or higher, preferably 9.2 or higher, and more preferably 10 or higher, at the time of or prior to the binding of proteins in a serum sample to the surface of the protein chip described above. This renders more accurate and simpler diagnosis of acute ischemic diseases, and selection of the timing to administer agents to subjects with such a disease and the optimal agents for treatment of subjects with such disease. The removal methods described above are not particularly limited. Samples that are suitable for the measurement of active hepcidin can be obtained, for example, by adsorption with chemical chips with immobilized cation exchange groups, such as CM10, at pH 8 to 10.

(4) Step of Measuring Protein Mass and Quantity

Mass numbers of proteins are measured by TOF-MS. When a pulsed UV laser is irradiated onto the protein chip after injection of the EAM, proteins ionized upon receiving the energy are accelerated through a constant voltage. The ionized protein travels toward the ion detector on the opposite side in the vacuum tube. The ion detector translates the detected ion information into the mass vs. charge ratio (mass-to-charge ratio, m/z). The signal intensity is also detected; thus, both protein mass and quantity can be determined. The "protein quantity" is assessed as a peak height on the data output screen. Such measurements can be achieved using ProteinChip (SELDI-TOF-MS, Ciphergen), AXIM-TOF$^2$ (MALDI-TOF-TOF, Shimadzu Co.), etc.

(5) Step of Analyzing Protein Expression

In general, SELDI-TOF-MS uses computers installed with measurement and analysis software. These computers can analyze data and display the number of detected proteins, the signal intensities and determined molecular weights of the detected proteins. Furthermore, the computer can display the data obtained in various formats. In the present invention, standard spectra can be displayed. It is possible to use useful formats, which include Biomarker Wizard (Ciphergen) and Biomarker Patterns® Software (BPS) (Ciphergen). Such analyses can be carried out using ProteinChip (SELDI-TOF-MS, Ciphergen), AXIM-TOF² (MALDI-TOF-TOF, Shimadzu Co.), etc.

The present invention also provides kits that are used in the test methods described above. The kits include, for example, protein chips and washing solutions to be used in the testing methods described above, instruction manuals, and the like.

In addition, the present invention provides compositions that are used in the methods of the present invention, which comprise polypeptides whose substantial pI is 8 or more and which are purified from samples collected from a subject. The noise in the measurement of active hepcidin can be reduced by using a "composition that comprises polypeptides whose substantial pI is 8 or more". This renders more accurate and simpler diagnosis of acute ischemic diseases, and selection of the timing to administer agents to subjects with such disease and the optimal agents for treatment of subjects with such a disease. Such compositions can produce a desired effect, as long as they comprise polypeptides with a pI greater than or equal to 8. The preferred pI is 9.2 or greater and a pI of 10 or higher is more preferred.

Furthermore, the "step of measuring the amount of active hepcidin in a sample collected from a subject" includes, for example, a method for quantitative analysis of peptides using LC-MS/MS. The method for quantitative analysis of peptides by LC-MS/MS enables simple and highly sensitive quantification of activated hepcidin. This renders more accurate and simpler tests for acute ischemic diseases, and selection of the timing to administer agents for treating subjects with this disease and the optimal agents for the treatment of subjects affected with this disease. For example, trichloroacetic acid is added to a sample collected from a subject, contaminants are precipitated by centrifugation after stirring, and the obtained supernatant is subjected to quantitative analysis of active hepcidin in the sample using a liquid chromatography/tandem mass spectrometer such as API 4000™ (Applied Biosystems).

All prior art documents cited in the specification are incorporated herein as reference.

EXAMPLES

The present invention is specifically described below with reference to the Examples; however, it is not to be construed as being limited thereto.

Example 1

1. Materials and Methods

From basic examination of various agents carried out with animal models of acute myocardial infarction so far (Mitsuma W., Biochem. Biophys. Res. Commun. 2006 Jun. 9; 344(3):987-94. Epub 2006 Apr. 19; Soda T., Int. J. Cardiol. 2007 Jan. 22; [Epub ahead of print.]; Ozawa T., J. Mol. Cell. Cardiol. 2006 May; 40(5):629-38; and Kato K., J. Jpn. Coll. Angiol, 2006,46:595-601), significant effect of reducing the infarct area was observed by administration of a formulation of erythropoietin (hereinafter abbreviated as EPO) which is a hematopoietic growth factor, whereas the effect was not observed at all in the EPO non-administration group. Thus, an EPO formulation was used for acute phase treatment of acute myocardial infarction patients.

The subjects were acute myocardial infarction patients within 24 hours of onset of one-vessel disease with ST-elevation, who are aged 80 or less and whose performance status was 0 to 3. The exclusion criteria were patients with multi-vessel disease, patients with Killip class III and IV or greater, patients with concomitant cardiogenic shock, patients with advanced kidney and/or liver diseases, patients with concomitant hypertension, and patients with abnormal Hct values of M>60% and F>55% upon blood collection during transcatheter intervention therapy. The therapeutic method involves comparing the prognoses of two groups: one subjected to no administration and the other subjected to one-shot administration of an EPO formulation under transcatheter conditions after transcatheter intervention. The therapeutic method was selected after obtaining patient consents, the two groups were assigned by random envelope assignment, and to avoid bias in case selection, pertinent cases that have developed within 24 hours were sequentially registered.

From serum samples collected at each point, the samples obtained 14 days after hospital entry were analyzed by proteomics using SELDI TOF-MS mass spectrometry.

SELDI-TOF-MS Analysis of Serum and Urine Proteins

For preliminary trials, multiple types of protein chips were used with various surface characteristics, which included weak cation exchange, strong anion exchange, and immobilized metal affinity capture for protein molecules that bind divalent cationic copper. The present inventor eventually chose the mobilized metal affinity capture ProteinChip® array (IMAC 30-Cu) for the entire study because of its reproducibility in detecting protein species from serum. SELDI analysis was performed according to the manufacturer's manual, with some modifications. In brief, serum samples were diluted 20-fold and 10-fold, respectively, with binding buffer (phosphate buffered saline, pH 7.4). Using a bioprocessor, 40 μl of diluted samples were applied onto different arrays of an IMAC 30-Cu chip pretreated with 100 mM copper sulfate binding buffer and the chip was incubated at room temperature for 30 min with constant horizontal shaking. For confirmation of the reproducibility, each sample was applied to two separate spots on an IMAC 30-Cu chip. Unbound proteins were removed by washing three times with binding buffer for 5 min. The arrays were rinsed twice with 400 μl of water, were air-dried, and 0.5 μl of alpha-cyano-4-hydroxycinnamic acid (CHCA; Ciphergen) in 50% acetonitrile and 0.5% trifluoroacetic acid was added twice onto the surface of the chip. Next, the arrays were analyzed using the Ciphergen ProteinChip® Reader PBS II. The proteins with CHCA were ionized and their molecular masses were determined by TOF analysis. The mass-to-charge ratio (m/z) of each of the proteins/peptides captured on the array surface was determined according to externally calibrated standards: Arg8-vasopressin (1,084.25 Da), somatostatin (1,637.9 Da), dynorphin (2,147.5 Da), bovine insulin beta-chain (3,495.94 Da), human insulin (5,807.65 Da), bovine ubiquitin (8,564.8 Da), and bovine cytochrome C (12,230.9 Da). The mass spectra of the samples were generated using an average of 80 laser shots at a laser intensity of 180 and a detector sensitivity of 10. Synthetic hepcidin-25 (Peptide Institute Inc, Osaka) was used as a marker of 2,789 Da. The peak intensity data were normalized with total ion current using Biomarker Wizard (Ciphergen ProteinChip® Software 3.1.1) to compensate for the variations in the concentration of samples loaded onto a spot.

2. Results

There were no characteristic items in the background of the 14 cases treated so far (Table 1).

TABLE 1

|  | Average |
| --- | --- |
| Blood count | |
| Hb(g/dl) | 13.3 |
| Ht(%) | 38.4 |
| WBC(ul) | 12321.4 |
| RBC(×10⁴/ul) | 424.9 |
| PLT(×10⁴/ul) | 24.0 |
| Ret(‰) | 1.1 |
| Vital | |
| SBP(mmHg) | 117.9 |
| DBP(mmHg) | 65.6 |
| PR | 82.5 |
| Biochemistry | |
| Alb(g/dl) | 3.8 |
| GOT(IU/l) | 151.6 |
| GPT(IU/l) | 43.3 |
| γ-GTP(IU/l) | 37.3 |
| HbA1c(%) | 5.5 |
| Na(mmol/l) | 139.1 |
| K(mEq/l) | 3.9 |
| CL(mmol/l) | 104.7 |
| LDH(U/l) | 454.8 |
| CPK(IU/l) | 1824.2 |
| TB(mg/dl) | 0.6 |
| BUN(mg/dl) | 15.3 |
| Cre(mg/dl) | 0.8 |
| TG | 59.3 |
| TP(g/dl) | 7.1 |
| UA(mg/dl) | 6.2 |

Figure 2:
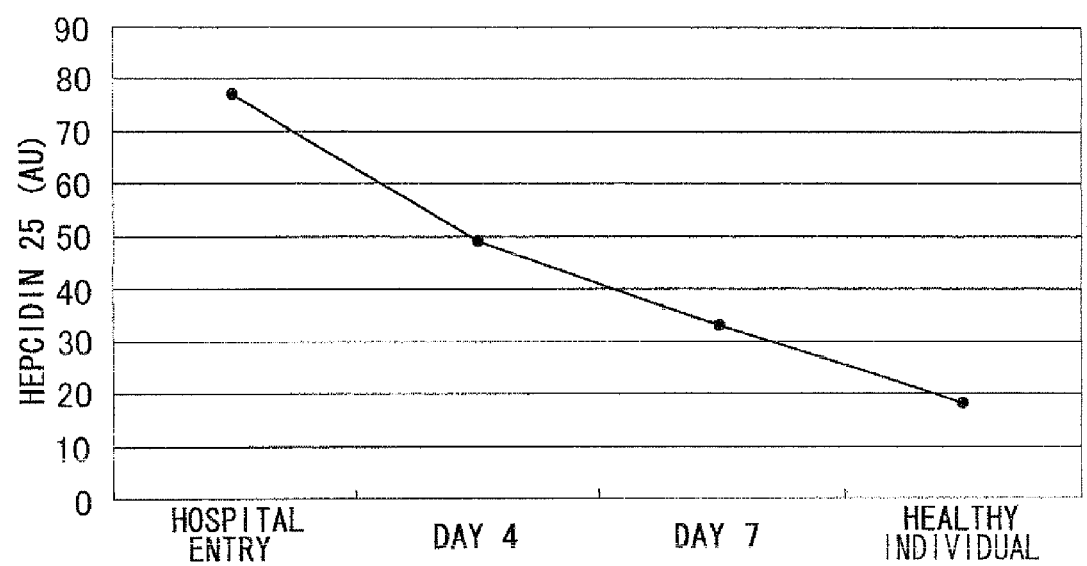
FIG. 2 shows the mean values for the time-dependent change of hepcidin-25 intensity in acute myocardial infarction patients.

The measured mean values for Hep20 were 136.24 AU (±107) at the time of blood collection before starting the treatment, and 28.7 AU (±52.7), 7.8 AU (±2.9), and 7.9 AU (±3.4), 4 days, 7 days, and 14 days after treatment, respectively, which decreased with the course of treatment and returned to the level of healthy individuals (7.5 AU±3.1) on day 14 (FIG. 1). The measured mean values for Hep25 were 81.4 AU (±80.3) at the time of blood collection before starting the treatment, and 50.6 AU (±43.4), 34.6 AU (±20.8), and 29.5 AU (±22.4), 4 days, 7 days, and 14 days after treatment, respectively, which decreased with the course of treatment, but contrary to the behavior of Hep20, did not return to the level of healthy individuals (18.1 AU±13.0) (FIG. 2).

Figure 3:
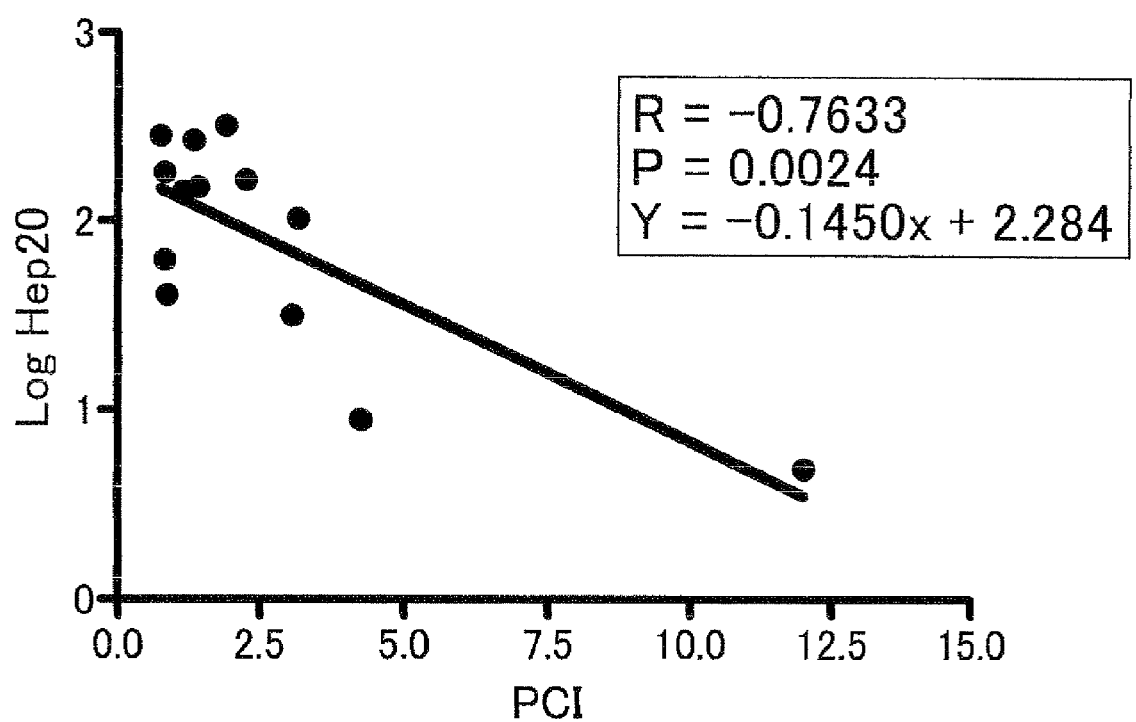
FIG. 3 shows the result of comparing the connection between Hep 20 and the time from the disease onset to initiation of treatment in acute myocardial infarction patients.

Furthermore, comparing the connection between Hep and the time from onset of the disease to initiation of treatment in 14 cases (FIG. 3) showed that the values of Hep20 were high 6 hours, particularly 4 hours, and furthermore 3.5 hours within onset.

3. Discussion

The current examination ascertained the elevation of Hep in the blood during infarction. This suggests that cardiac muscles contain appreciable amounts of iron, but during infarction, this iron causes spreading of the infarct area and tissue breakdown during ischemia reperfusion. In particular, the behavior of hepcidin 20 in the blood is considered to directly represent damage of the cardiac muscles, and this enables determination of the degree of recovery from cardiac muscle damage, or more specifically the therapeutic effect by therapy after ischemia and reperfusion. The current examination suggested that with the treatment of acute ischemic heart disease, in particular, acute myocardial infarction, serial measurements of Hep in the blood are effective, and that Hep in the blood may become very effective as a therapeutic marker for acute ischemic heart disease and a very effective marker for learning the degree of damage on cardiac muscles in acute ischemia. In particular, since the blood level of Hep20 within six hours of disease onset is very high, early diagnosis of acute ischemic heart disease is possible by using Hep 20 as a marker.

INDUSTRIAL APPLICABILITY

The present invention provides methods for diagnosing acute ischemic diseases using active hepcidin as an indicator. It has been found that the expression level of hepcidin mRNA does not correlate with the hepcidin protein concentration in blood, and acute ischemic diseases cannot be diagnosed accurately by methods that do not directly measure the concentration of hepcidin protein in blood, for example, disease diagnostic methods that measure the amount of hepcidin mRNA expression. However, the present method enables more accurate, clinically relevant diagnosis of acute ischemic diseases and determination of the timing of administration and dose of therapeutic agents for acute ischemic diseases.

Furthermore, at the time of disease onset, since the blood concentration of hepcidin-20 rises sharply in particular and shows high levels 6 hours, especially 4 hours, and furthermore 3.5 hours within onset, the present invention enables early diagnosis of acute ischemic diseases. Particularly with myocardial infarction in diabetes patients and such, symptoms such as pain are rare and diagnosis has been difficult. However, the disease can be diagnosed easily also in the case of such patients who can then be treated at an early stage.

Thus, acute ischemic diseases can be diagnosed at an earlier stage by using kits used for the diagnostic methods of the present invention.

The invention claimed is:

1. A method of testing for an acute ischemic heart disease, which comprises (a) measuring the amount of hepcidin-20 and/or hepcidin-25 in a sample collected from a subject suspected of having the acute ischemic heart disease, and (b) correlating an elevated level of hepcidin-20 and/or hepcidin-25 with said acute ischemic heart disease.

2. A method for determining the timing of administration of an agent for treating an acute ischemic heart disease, which comprises (a) measuring the amount of hepcidin-20 and/or hepcidin-25 in a sample collected from a subject having the acute ischemic heart disease, and (b) administering the agent when an elevated level of hepcidin-20 and/or hepcidin-25 is detected in said subject.

3. The method of claim 1, wherein the amount of hepcidin-20 is measured in step (a) and an elevated level of hepcidin-20 is correlated with said acute ischemic heart disease in step (b).

4. The method of claim 1, wherein the acute ischemic heart disease is acute myocardial infarction.

5. The method of claim 1, wherein the sample collected from the subject is selected from the group consisting of plasma, serum, blood, urine, and tissue extract.

6. The method of claim 2, wherein the amount of hepcidin-20 is measured in step (a) and administering the agent when an elevated level of hepcidin-20 is detected.

7. The method of claim 2, wherein the acute ischemic heart disease is acute myocardial infarction.

8. The method of claim 2, wherein the sample collected from the subject is selected from the group consisting of plasma, serum, blood, urine, and tissue extract.

9. The method of claim 1, wherein the level of hepicidin-20 and/or hepicidin-25 of the sample is compared with a level of hepicidin-20 and/or hepicidin-25 of a control sample, respectively.

10. The method of claim 1, wherein the subject has an acute myocardial infarction.

* * * * *

UNITED STATES PATENT AND TRADEMARK OFFICE
CERTIFICATE OF CORRECTION

PATENT NO. : 8,187,827 B2
APPLICATION NO. : 12/601955
DATED : May 29, 2012
INVENTOR(S) : Naohisa Tomosugi It is certified that error appears in the above-identified patent and that said Letters Patent is hereby corrected as shown below:

Column 3, line 22, insert:

-- Patent Document 4: US 2006/0019339 A1 --

Signed and Sealed this
Tenth Day of July, 2012

David J. Kappos
*Director of the United States Patent and Trademark Office*